United States Patent
Knol et al.

(10) Patent No.: US 9,498,523 B2
(45) Date of Patent: *Nov. 22, 2016

(54) BIFIDOBACTERIUM FOR DUST MITE ALLERGY

(71) Applicant: N.V. NUTRICIA, Zoetermeer (NL)

(72) Inventors: Jan Knol, Wageningen (NL); Leon Matthieu Johannes Knippels, Utrecht (NL); Dominique Anne Marie Goossens, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/788,521

(22) Filed: Jun. 30, 2015

(65) Prior Publication Data

US 2015/0297703 A1    Oct. 22, 2015

Related U.S. Application Data

(63) Continuation of application No. 12/746,584, filed as application No. PCT/NL2008/050781 on Dec. 8, 2008, now Pat. No. 9,119,414.

(51) Int. Cl.
| | |
|---|---|
| *A61K 39/05* | (2006.01) |
| *A23L 1/30* | (2006.01) |
| *A61K 35/745* | (2015.01) |
| *A61K 39/39* | (2006.01) |
| *A61K 39/00* | (2006.01) |

(52) U.S. Cl.
CPC .............. *A61K 39/05* (2013.01); *A23L 1/3014* (2013.01); *A61K 35/745* (2013.01); *A61K 39/39* (2013.01); *A23V 2002/00* (2013.01); *A23Y 2300/29* (2013.01); *A61K 2039/52* (2013.01); *A61K 2039/542* (2013.01); *A61K 2039/55583* (2013.01)

(58) Field of Classification Search
None
See application file for complete search history.

(56) References Cited

U.S. PATENT DOCUMENTS

| | | | | |
|---|---|---|---|---|
| 8,591,919 B2 * | 11/2013 | Stahl | ........................ | A23L 1/296 424/278.1 |
| 9,119,414 B2 * | 9/2015 | Knol | ...................... | A23L 1/3014 |
| 2003/0133921 A1 | 7/2003 | Ohishi et al. | | |
| 2004/0071685 A1 | 4/2004 | Houston et al. | | |
| 2007/0207132 A1 * | 9/2007 | Speelmans | .............. | A23L 1/296 424/93.45 |
| 2009/0136468 A1 | 5/2009 | Speelmans et al. | | |
| 2010/0278781 A1 * | 11/2010 | Hougee | ................. | A23L 1/3014 424/93.4 |
| 2011/0014156 A1 | 1/2011 | Knol et al. | | |
| 2011/0097437 A1 | 4/2011 | Knol et al. | | |
| 2011/0117077 A1 | 5/2011 | Schmitt et al. | | |
| 2011/0150851 A1 | 6/2011 | Schmitt et al. | | |
| 2011/0182934 A1 | 7/2011 | Potappel-van 'T Land et al. | | |
| 2012/0141541 A1 | 6/2012 | Stahl et al. | | |
| 2014/0335073 A1 | 11/2014 | Knol et al. | | |

FOREIGN PATENT DOCUMENTS

| | | |
|---|---|---|
| EP | 1230931 A1 | 8/2002 |
| WO | 2005039319 A2 | 5/2005 |
| WO | 2006091103 A2 | 8/2006 |

OTHER PUBLICATIONS

Moro G et al. Arch Disease Childhood 91(10); 814-819 Oct. 2006.
Bunselmeyer B, Hautarzt 57(9):785-791 Sep. 2006 (German Lang) (English language abstract attached).
Rosenfeldt V et al. J Allergy Clin Immunol. 111(2): 389-395 Feb. 1, 2003.
Vos AP et al. Pediatric Aller Immunol. 18(4): 304-312, Jun. 2007.
Ogawa T et al. FEMS Immunol Med Microbiol 46(3):400-409 Apr. 1, 2006.
Hisbergues M et al. Clin Exper Allergy 37(9): 1286-1295 Sep. 2007.
Charng Y-C et al.Vaccine 24(33-34): 5931-5936 Aug. 14, 2006.
Van Laere, Katrien M. J. "Degradation of Structurally Different Non-Digestible Oligosaccharides by Intestinal Bacteria: Glycosylhydrolases of Bifidobacterium adolescentis" Doctoral Thesis, Wageningen University, 2000, 152 pages.
Vallance, G, et al. "House Dust Mite Control Measures in the Treatment of Asthma," Ther. Clin. Risk Management 2 (4):347-354 (Dec. 15, 2006).

* cited by examiner

*Primary Examiner* — Thane Underdahl
*Assistant Examiner* — Aaron J Kosar
(74) *Attorney, Agent, or Firm* — Browdy and Neimark, PLLC

(57) ABSTRACT

A composition comprising *Bifidobacterium breve* for use in improving lung function in human subjects suffering from dust mite allergy.

16 Claims, No Drawings

BIFIDOBACTERIUM FOR DUST MITE ALLERGY

FIELD OF THE INVENTION

The invention is in the field of treatment and/or prevention of dust mite induced respiratory insufficiency.

BACKGROUND OF THE INVENTION

House dust mite (*Dermatophagoides*) allergy is a hypersensitive reaction to proteins present in the excretion products of house dust mites and can result in respiratory insufficiencies such as airway obstruction and bronchial hyperreactivity. Such hypersensitive reaction is called "dust mite induced respiratory insufficiency" in the present document. House dust mites are found in almost all homes. The excretion products of dust mites can form a serious threat to those sensitive to said excretion products as well as to critically ill patients. The dust mites are not visible to the unaided eye, and thus difficult to detect in the house.

In the study by Mihrishahi et al. (J Allergy Clin Immunol, 2003; 111:162-8) no benefit on symptoms by actively avoiding house dust mite was found. Presently an important treatment of dust mite induced respiratory insufficiency is symptom prevention by the administration of e.g. bronchodilators.

From several studies in the last years it is now suggested that there is a role for probiotics in the management of food allergic disease in infants. WO 2005/039319 discloses the use of *B. breve* with non-digestible oligosaccharides for normalisation of the *Bifidobacterium* population on a species level in non-breast fed infants.

DE 102006005404 discloses the use of immune modifying gram positive bacteria for the use of allergy.

EP 1 230 932 discloses transformed bacteria of the genus *Lactobacillus* or *Streptococcus*, the bacteria having a DNA molecule that includes (1) a nucleotide sequence that encodes a protein allergen and (2) a promoter operably linked to the nucleotide sequence.

WO 2007/105945 discloses a food or supplement for pregnant women comprising water soluble, non-digestible saccharides, to improve the flora and/or immune system and to improve the intestinal flora of the infant after birth.

WO2006/123230 discloses an immunogenic composition, comprising at least an antigen and at least an adjuvant that is a bacterium selected from a *Bifidobacterium* and a lactic acid bacterium, to elicit antigen-specific immune tolerance.

SUMMARY OF THE INVENTION

It has now surprisingly been found that a composition comprising *Bifidobacterium breve* effectively reduces the allergic reaction to the excrements of house dust mites, particularly dust mite induced respiratory insufficiency.

It has been found that the composition of the present invention beneficially affects peak expiratory flow rate in adult patients with house dust mite (HDM) IgE-mediated allergic asthma. Also the IL-5 release after provocation with house dust mite was suppressed in adult patients administering the composition of the present invention.

DETAILED DESCRIPTION OF THE INVENTION

The present invention relates to a method for treatment and/or prevention of dust mite allergy and/or dust mite induced respiratory insufficiency in a human, said method comprising administering a composition comprising non-genetically modified *Bifidobacterium breve* to said human. In other words the present invention relates to the use of a non-genetically modified *Bifidobacterium breve*, for the manufacture of a composition for treatment and/or prevention of dust mite allergy and/or dust mite induced respiratory insufficiency in a human. The present invention can also be worded as a composition comprising a non-genetically modified *Bifidobacterium breve* for treatment and/or prevention of dust mite allergy and/or dust mite induced respiratory insufficiency in a human.

In another embodiment the present invention concerns a method to increase peak expiratory flow rate in a human subject suffering from allergy and/or asthma, said method comprising administering a composition comprising non-genetically modified *Bifidobacterium breve* to said human. In other words the present invention relates to the use of a non-genetically modified *Bifidobacterium breve*, for the manufacture of a composition for increasing peak expiratory flow rate in a human subject suffering from allergy and/or asthma. The present invention can also be worded as a composition comprising a non-genetically modified *Bifidobacterium breve* for increasing peak expiratory flow rate in a human subject suffering from allergy and/or asthma.

Dust Mite Induced Respiratory Insufficiency

The term dust mite in the present invention also relates to house dust mite or house mite or mites belonging to the genus *Dermatophagoides*. The present invention provides composition and a method for the treatment and/or prevention of dust mite allergy, particularly dust mite induced respiratory insufficiency, particularly dust mite excrement induced respiratory insufficiency. Especially dust mite induced asthma and dust mite induced inflammatory diseases of the lung can be treated and/or prevented. Dust mite induced asthma can be described as immediate phase with bronchoconstriction, to chronic state with bronchial eosinophiles infiltration and hypersecretion. An example of dust mite induced inflammatory diseases of the lung is dust mite induced rhinitis.

Dust mite induced disease, e.g. dust mite induced respiratory insufficiency, is sometimes also referred to as dust induced allergic reaction. Dust mite induced respiratory insufficiencies which can be suitably treated and/or prevented include dust mite induced difficulty in breathing, dust mite induced heavy breathing, dust mite induced respiratory tract infection, dust mite induced irritation in the lungs, dust mite induced congestion in the lungs, dust mite induced excessive mucus production, dust mite induced breathlessness, dust mite induced bronchitis, dust mite induced bronchiolitis, dust mite induced tracheitis, dust mite induced pneumonia, dust mite induced sinusitis, dust mite induced airflow obstruction and/or dust mite induced rhinitis.

Peak expiratory flow rate (PEFR) is the maximum flow generated during expiration. PEFR is usually measured when performed with maximal force and started after a full inspiration. PEFR is a test which determines how well the lungs work. A suitable method to measure PEFR is described in Quanjer et al., 1997, *Eur. Respir. J* 10 *Suppl* 24:2s-8s. Increasing PEFR in a human subject means that a statistically significant increase in the PEFR is observed in a treatment group receiving the present *B. breve* containing composition compared to the values before treatment. Preferably the increase is at least 5%, more preferably at least 10%.

Bifidobacterium Breve

Immune effects of bacteria are highly species and/or strain specific. Therefore the inventors have performed extensive preclinical work in the field of identifying the most effective and safe species to be used as probiotic bacteria in the diet of dust mite allergic patients. The selected probiotic species according to the present invention had superior effects regarding bronchial hyperresponsiveness and bronchial inflammation in an ovalbumin allergy mouse model, compared to probiotic strains of other species. Furthermore, selected probiotic according to the present invention were tested in various in vitro assays and animal models regarding safety and found to be superior to other probiotic strains belonging to other species.

The present composition comprises non-genetically modified *Bifidobacterium breve*. *Bifidobacterium breve* is a Gram-positive, anaerobic, branched rod-shaped bacterium. The present *B. breve* preferably has at least 95% identity of the 16 S rRNA sequence when compared to the type strain of *B. breve* ATCC 15700, more preferably at least 97% identity (Stackebrandt & Goebel, 1994, *Int. J. Syst. Bacteriol.* 44:846-849). Preferred *B. breve* strains are those isolated from the faeces of healthy human milk-fed infants. Typically, these are commercially available from producers of lactic acid bacteria, but they can also be directly isolated from faeces, identified, characterised and produced. According to a preferred embodiment, the present composition contains at least one *B. breve* selected from the group consisting of *B. breve* Bb-03 (Rhodia/Danisco), *B. breve* M-16V (Morinaga), *B. breve* R0070 (Institute Rosell, Lallemand), *B. breve* BRO3 (Probiotical), *B. breve* BR92) (Cell Biotech), DSM 20091, LMG 11613, YIT4065, FERM BP-6223 and CNCM I-2219. Most preferably, the *B. breve* is selected from the group consisting of *B. breve* M-16V and *B. breve* CNCM I-2219.

The present composition preferably contains $10^2$ to $10^{13}$ colony forming units (cfu) *B. breve* per gram dry weight of the present composition, preferably $10^4$ to $10^{12}$, more preferably $10^5$ to $10^{10}$, most preferably from $10^5$ to $1 \times 10^9$ cfu *B. breve* per gram dry weight of the present composition. The dose of *B. breve* according to the present invention is preferably administered at a daily dose of $10^2$ to $10^{13}$, more preferably from $10^5$ to $10^{12}$, most preferably from $10^8$ to $5 \times 10^{10}$ colony forming units (cfu).

The present composition preferably comprises viable *B. breve*. Alternatively, the present composition preferably comprises non-viable *B. breve* equivalent to the amounts of CFU as described above. The equivalent of cfu can be determined by performing the 5'nuclease assay with the *B. breve* probes and primers as disclosed in WO 2005/039319 in the product (i.e., an infant formula) comprising non-viable *B. breve* and compare this with a calibration curve obtained from a comparable product (for instance a standard infant formula) to which known amounts of dried, viable *B. breve* cfu have been added. The dried viable bifidobacteria can be commercially obtained as described above. *B. breve* cells can be made non-viable by methods known in the art, including heat treatment steps (including sterilization, pasteurization, UHT treatment), radiation (UV), treatment with oxygen, treatment with bactericidals such as ethanol, sonication, ultra high pressure application, high pressure homogenization and use of a cell disruptor. Preferably the *B. breve* is heat-killed. The presence of non-viable *B. breve* advantageously provides many product technological benefits, including increased shelf-life, a reduced incidence of bacterial contamination, decreased post-acidification of the product, improved dosage control and improved convenience of reconstitution.

The *B. breve* of the present invention is not genetically modified. Genetic modification is disadvantageous with respect to safety and consumer acceptance. Furthermore, generic modification is costly and usually negatively affects strain growth properties. Hence, *Bifidobacterium breve* strain expressing, via recombination techniques known in the art, the antigen of dust mites are not part of the present invention.

Non-Digestible Oligosaccharides

The present composition preferably comprises non-digestible oligosaccharides which are fermented into organic acids (preferably lactic acid, butyrate, propionate and/or acetate) and stimulate the growth of the intestinal lactic acid producing bacteria (hereinafter referred to as "non-digestible saccharides"). Preferably the growth of bifidobacteria and/or lactobacilli is stimulated, more preferably bifidobacteria, most preferably growth of *B. breve* is stimulated. An increased content of bifidobacteria and/or lactobacilli stimulate the formation of a healthy intestinal flora. The non-digestible oligosaccharides also enhance the effectiveness of the *B. breve* in the present composition, as co-administration of the non-digestible oligosaccharides with the *B. breve* selectively stimulates the growth of *B. breve* in the gastrointestinal tract and/or improves the survival of *B. breve* in the product.

The non-digestible oligosaccharides are preferably not or only partially digested in the intestine by the action of acids or digestive enzymes present in the human upper digestive tract (small intestine and stomach) and are fermented by the human intestinal flora. For example, sucrose, lactose, maltose and the maltodextrins are considered digestible.

The present composition preferably comprises non-digestible oligosaccharides. Preferably the present composition comprises non-digestible oligosaccharides with a DP between 2 and 250, more preferably 2 to 60. The non-digestible oligosaccharide is preferably at least one, more preferably at least two, selected from the group consisting of fructo-oligosaccharides (including inulins), galacto-oligosaccharides (including transgalacto-oligosaccharides), xylo-oligosaccharides, arabino-oligosaccharides, arabinogalacto-oligosaccharides, gluco-oligosaccharides (including cyclodextrins, gentio- and nigero-oligosaccharides and non-digestible polydextrose), chito-oligosaccharides, glucomanno-oligosaccharides, galactomanno-oligosaccharides (including partially hydrolyzed guar gum), mannan-oligosaccharides, fuco-oligosaccharides, sialic acid comprising oligosaccharides, uronic acid oligosaccharides, (including galcturonic acid oligosaccharides and pectin degradation products). More preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of inulin and fructo-oligosaccharides. In a preferred embodiment the composition comprises galacto-oligosaccharides and/or fructo-oligosaccharides. In a preferred embodiment the composition comprises a mixture of galacto-oligosaccharides and a fructooligosaccharides selected from the group consisting of short chain fructo-oligosaccharides and inulin, more preferably inulin. A mixture of at least two different non-digestible oligosaccharides advantageously stimulates the beneficial bacteria of the intestinal microbiota to a greater extent. Preferably the weight ratio in a mixture of the two different non-digestible oligosaccharides, preferably galacto-oligosaccharides and fructooligosaccharide, is between 25 and 0.05, more preferably between 20 and 1. Galactooligosaccharides are more capable of stimulating bifidobacteria. Preferably the present composition comprises galacto-oligosaccharides with a DP of 2-10 and/or fructo-oligosaccharides with a DP of 2-60.

The galacto-oligosaccharide is preferably selected from the group consisting of transgalacto-oligosaccharides, lacto-N-tetraose (LNT), lacto-N-neotetraose (neo-LNT), fucosyllactose, fucosylated LNT and fucosylated neo-LNT. In a particularly preferred embodiment the present composition comprises transgalacto-oligosaccharides ([galactose]n-glucose; wherein n is an integer between 1 and 60, i.e., 2, 3, 4, 5, 6, . . . , 59, 60; preferably n is selected from 2, 3, 4, 5, 6, 7, 8, 9, or 10), wherein the galactose units are linked together via a beta linkage. Transgalacto-oligosaccharides (TOS) are for example sold under the trademark Vivinal™ (Borculo Domo Ingredients, Netherlands). Preferably the saccharides of the transgalacto-oligosaccharides are beta-linked Fructo-oligosaccharide is a NDO comprising a chain of beta-linked fructose units with a DP or average DP of 2 to 250, more preferably 2 to 100, even more preferably 10 to 60. Fructo-oligosaccharide includes inulin, levan and/or a mixed type of polyfructan. An especially preferred fructo-oligosaccharide is inulin. Fructo-oligosaccharide suitable for use in the compositions is also commercially available, e.g., RaftilineHP® (Orafti). Uronic acid oligosaccharides are preferably obtained from pectin degradation products. Hence the present composition preferably comprises a pectin degradation product with a DP between 2 and 100. Preferably the pectin degradation product is prepared from apple pectin, beet pectin and/or citrus pectin. Preferably the composition comprises transgalacto-oligosaccharide, fructo-oligosaccharide and a pectin degradation product. The weight ratio transgalacto-oligosaccharide:fructo-oligosaccharide:pectin degradation product is preferably (20 to 2):1:(1 to 20), more preferably (20 to 2):1:(1 to 10), even more preferably (20 to 2):1:(1 to 3), even more preferably (12 to 7):1:(1 to 2).

Preferably, the composition comprises 80 mg to 2 g non-digestible oligosaccharides per 100 ml, more preferably 150 mg to 1.50 g, even more preferably 300 mg to 1 g non-digestible oligosaccharides per 100 ml. Based on dry weight, the composition preferably comprises 0.25 wt % to 5.5 wt % non-digestible oligosaccharides, more preferably 0.5 wt % to 4 wt %, even more preferably 1.5 wt % to 3 wt %. A lower amount of non-digestible oligosaccharides will be less effective in stimulating the beneficial bacteria in the microbiota, whereas a too high amount will result in side-effects of bloating and abdominal discomfort.

Preferably, the present composition comprises $10^4$ to $10^{12}$, more preferably from $10^5$ to $10^{11}$, most preferably from $10^7$ to $5 \times 10^{10}$ colony forming units (cfu) *B. breve* per g of the total of non-digestible oligosaccharides.

Subjects

The present composition is particularly suitable for treatment and/or prevention of dust mite allergy and/or dust mite induced respiratory insufficiency in human children with the age between 0 and 10 years, preferably infants with the age between 0 and 4 years. The present composition is particularly suitable for treatment and/or prevention of dust mite allergy and/or dust mite induced respiratory insufficiency in human adults. The present composition is particularly suitable for treatment and/or prevention of dust mite induced respiratory insufficiency in human subjects. The present composition is particularly suitable for increasing of peak expiratory flow rate in human children with the age between 0 and 10 years, preferably infants with the age between 0 and 4 years, suffering from allergy and/or asthma, more particular dust mite allergy and/or dust mite induced asthma. The present composition is particularly suitable for increasing of peak expiratory flow rate in human adult subjects suffering from dust mite allergy and/or dust mite induced asthma more particular dust mite allergy and/or dust mite induced asthma.

Additionally, the present composition can be advantageously used by patients likely to develop a respiratory tract infection disease, particularly patients infected with human immunodeficiency virus (HW) and/or persons suffering from one or more of the following diseases: nephrotic syndrome, multiple myeloma, lymphoma, Hodgkin's disease, persons which have undergone organ transplantation, persons with chronic illnesses of the hart, kidney or lungs (especially chronic obstructive pulmonary disease (COPD), lung emphysema, sarcoidosis, cystic fibrosis, bronchiectasis, lung cancer, atelectasis, respiratory failure, occupational lung diseases, asthma, eosinophily), diabetes, alcoholism, dysphagia, and gastro-oesophagal reflux disease.

In a further preferred embodiment, the present invention comprises the administration of the present composition to patients, particularly patients that are on a ventilator or artificial breathing machine and patients in the intensive care unit. These patients are particularly vulnerable for inflammatory diseases and infections.

In the prior art results have mainly been obtained in infants, which have a flora and an immune system which is easier to manipulate, instead of in adults with an established flora and immune system, which is less easy to change. It has surprisingly been found that *B. breve* reduces the allergen-induced response in allergic patients with established asthma by reducing the systemic production of Th2-type cytokines IL-4, IL-5 and/or IL-13. The composition according to the invention reduces the allergen-induced response in allergic patients by reducing the systemic production of Th2-type cytokines IL-4, IL-5 and/or IL-13. The composition according to the invention reduces IL-4 and/or IL-5 and/or IL-13.

Nutritional Composition and Mode of Administration

The composition used in the present method is preferably administered enterally, more preferably orally.

In a preferred embodiment the present composition is administered as, or is comprised in, a nutritional matrix, said nutritional matrix preferably containing a lipid, a protein and a carbohydrate component. This is particularly critical for infants who cannot yet swallow capsules. Hence, for infants with the age between 0 and 4 years, preferably the present *Bifidobacterium breve* is embedded in a nutritional composition containing fat, carbohydrates and protein. In a preferred embodiment the present nutritional composition fulfills, or the present method comprises the administration of a nutritional composition which fulfills, the requirements for feeding infants, particularly nutritional compositions containing between 10 and 60 en-% lipid, between 5 and 50 en-% protein, between 15 and 90 en-% carbohydrate. More preferably the nutritional composition comprises between 7.5 to 12.5 en-% protein, 40 to 55 en-% carbohydrates, and 35 to 50 en-% fat. (en-% is short for energy percentage and represents the relative amount each constituent contributes to the total caloric value of the preparation).

The present nutritional composition preferably comprises at least 0.1 wt. %, preferably at least 0.25 wt. %, more preferably at least 0.5 wt. %, even more preferably at least 0.75 wt. % LC-PUFA with 20 and 22 carbon atoms of the total fat content. The content of LC-PUFA with 20 and 22 carbon atoms in the present composition, preferably does not exceed 15 wt. % of the total fat content, preferably does not exceed 10 wt. %, even more preferably does not exceed 5 wt. % of the total fat content. LC-PUFA beneficially affect dust mite allergy and/or dust mite induced respiratory insufficiencies.

According to a further preferred embodiment, the present composition is in the form of, or is ingested in the form of, a powder, a capsule, pill or tablet (hereinafter unit dosage). This has the advantage that the diet of the subject does not have to be changed, and the *B. breve* comprising supplement can be ingested in addition to the normal diet. Furthermore, by choosing a sachet or a capsule as the form of administration *B. breve* can suitably be protected from air and moisture, which beneficially affects the viability of the bacteria and/or the shelf life of the product. The unit dosage preferably has a weight between 0.1 and 15 grams per unit. The unit dosages preferably comprises at least $1 \times 10^8$ cfu *Bifidobacterium breve*.

EXAMPLES

Example 1

Sachets with Synbiotics

A sachet comprising 10 g of which
A. *Bifidobacterium Breve* strain M-16V (Morinaga), $1 \times 10^{10}$ cfu in 0.1 g,
B. 4 g GOS/FOS mixture w/w 9/1, as a source of GOS Vivinal GOS (DOMO Borculo) and as a source of FOS RaftilineHP® (Tiense) was used
C. The rest being maltodextrin.

Example 2

Effect of Oral Treatment with Probiotic Bacteria in Adult Patients with House Dust Mite (HDM) IgE Mediated Allergic Asthma A group of 30 adult patients that suffered from mild to moderate asthma and a known HDM IgE mediated allergy to house dust mite (according to the American Thoracic Society Criteria) were included. Patients were randomised in a double-blind parallel design to receive a supplement according to example 1 (Group A) or a placebo supplement comprising maltodextrin (group B) twice daily for a period of 4 weeks. Sachets were dissolved in cold drinks, yoghurt or custard.

At study entry and after the four weeks of intervention, allergen challenge was performed, which took 3 days. On day 1 a blood sample was taken after which the histamine provocation test was performed. After the histamine provocation test sputum was collected. On day 2 the allergen provocation test was performed during which sputum and blood samples were collected. On day 3 a blood sample was taken after which the histamine provocation test was performed. After the histamine provocation test sputum was collected. Peak expiratory flow rates (PEFR) were measured by the subjects themselves twice a day, in the morning and evening, throughout the 4 weeks study period using a portable PEF meter.

Bronchial inflammation was determined using the collected sputum (Eosinophils, neutrophils, Eosinophil cationic protein (ECP), Myeloperoxidase (MPO)).

Immunological parameters were determined in the blood samples: Number of eosinophilic granulocytes, IL-5, Total and Der p 1 specific IgE, IgG1 and IgG4, $T_{reg}$ cells: CD4/CD25/CD103/GITR/FoxP3, IL-4, IL-5, IL-10, IFN-γ, MIG, IP-10, IL-12p70, IL-13, TGF-β and IL-18 Elispot assay: Th1/Th2 ratio based on IL-4 and IFN-γ or on IL-4 and IL-13.

Bronchial responsiveness was determined measuring lung function, responsiveness to allergen and histamine and peak expiratory flow rates.

The results of the two formula groups were evaluated using t-tests for parametric data and by the Mann-Whitney test for non-parametric data. Binary and categorical data were assessed by chi-squared analyses.

Bronchial exposure to house dust mite (HDM) caused an immediate decline in FEV1 of at least 20% in all subjects. Most subjects also experienced a late asthmatic reaction (LAR) several hours after inhalation of the last dose of HDM. A small difference in lung function during the LAR between both treatment groups after intervention was observed The difference in mean AUC from 2 to 6 hours after challenge was +2.3 in group B vs −3.5 after treatment in group A.

The results on expiratory flow are shown in Table 1. A statistically significant (p=0.003 for the morning measurements and p=0.011 for the evening measurements) increase in peak expiratory flow rate was observed in the group administered the *B. breve* compared to the placebo group. The results on IL-5 are shown in Table 2. After intervention, a statistically significant suppression of IL-5, released upon allergen provocation, (p=0.06 after 6 h and p=0.019 after 24 h), was found compared to the control group. Before intervention the IL-5 release induced by allergen provocation was the same in both groups.

Consistent with the changes in IL-5 production, we found no significant increase in the amount of Th2 cytokines (IL-4 and IL-13), produced by HDM-stimulated PBMCs in group A as opposed to that in group B (p=0.046 for the total of Th2 cytokines), see Table 3.

TABLE 1

Peak Expiratory Flow Rate (liter/minute) measured in the morning or evening, corrected for baseline value.

| Group | Time | Week 2 | Week 3 | Week 4 |
|---|---|---|---|---|
| A | Morning | 15.06 | 15.83 | 20.29 |
|   | Evening | 15.06 | 15.83 | 20.29 |
| B | Morning | 4.43 | 0.43 | −2.24 |
|   | Evening | −2.11 | −5.09 | −10.49 | a: The values at week 1 were taken as the base line value

TABLE 2

IL-5 effects (pg/ml) after intervention during allergen provocation with HDM antigen

| Group | t = 0 | t = 6 h | t = 24 h |
|---|---|---|---|
| A | 1.35 | 12.65 | 36.31 |
| B | 2.66 | 22.56 | 67.81 |

TABLE 3

IL-4 and IL-13 (pg/ml) effects after intervention during
allergen provocation with 5 µg/ml HDM antigen

| Group | | Time during Provocation Procedure | |
|---|---|---|---|
| | | t = 0 | t = 24 h |
| A | IL-4 | 6.4 | 6.6 |
| | IL-13 | 2.7 | 2.9 |
| B | IL-4 | 5.0 | 7.1 |
| | IL-13 | 2.0 | 2.7 |

A significant increase at 6 and 24 hours after allergen challenge in the number of eosinophils and the amount of ECP in the induced sputum samples was observed. Neutrophil counts and MPO levels in sputum were also increased at both time points after allergen challenge. The increase in these sputum inflammatory parameters during the LAR was slightly decreased in group A compared to group B after intervention at t=6. See table 4. At t=24 levels were returned to the values observed at t=24 before intervention (data not shown).

TABLE 4

Sputum inflammatory parameters after intervention

| | | Group A | Group B |
|---|---|---|---|
| Eosinophils ($\times 10^4$/g) | t = −24 | 1.4 | 1.8 |
| | t = 6 | 10.72 | 19.3 |
| Neutrophils ($\times 10^4$/g) | t = −24 | 18.8 | 20.6 |
| | t = 6 | 32.2 | 42.3 |
| ECP (ng/g) | t = −24 | 19 | 15 |
| | t = 6 | 73 | 87 |
| MPO (ng/g) | t = −24 | 323 | 356 |
| | t = 6 | 562 | 636 |

Values are expressed as geometric mean (SE) per gram sputum.
ECP = eosinophil cationic protein,
MPO = Myeloperoxidase.

These results are indicative for the beneficial effects of a composition comprising *B. breve* in humans suffering from dust mite allergy and/or dust mite induced respiratory insufficiency. These results are indicative for the beneficial effects of a composition comprising *B. breve* on lung function in humans suffering from asthma and/or allergy.

As IL-4 and IL-13 are important Th2-mediators in the class switching of B cells to produce allergen-specific IgE that binds to the high-affinity receptor for IgE on mast cells, basophils and activated eosinophils, and IL-5 directs the recruitment and activation of eosinophils, reduction of these cytokines as a result of treatment with *B. breve* eventually leads to a reduced allergic inflammatory response.

In contrast to several human studies that suggest an increase in regulatory cytokines (IL-10) or regulatory T cells after probiotic treatment, no indication was found that the immunomodulatory effect of *B. breve* was mediated by the induction of or a change in regulatory properties. So, *B. breve* do not seem to affect sensitization to allergens per se, but may regulate the path from sensitization to clinical disease; in this case, by reducing the production of Th2-type cytokines, the allergic response after allergen encounter will decline over time. Eventually, after prolonged treatment, and thus reduction of Th2 response for a longer period, also the allergic inflammation in the airways will decline and thereby result in improved lung function. In this study, already an improvement in PEF was observed in group A.

This is the first study that shows that *B. breve* reduces the allergen-induced response in allergic patients with established asthma by reducing the systemic production of Th2-type cytokines IL-4, IL-5 and IL-13.

What is claimed is:

1. A method for treating dust mite allergy or dust mite-induced asthma and/or dust mite-induced respiratory insufficiency in a human subject in need thereof, comprising administering to said subject an effective amount of a composition that comprises, based on dry weight of the composition:
    (a) at least $10^4$ cfu per gram *Bifidobacterium breve* bacteria that are not genetically modified, and
    (b) 0.25 to 5.5 wt % non-digestible oligosaccharides that include inulin and fructo-oligosaccharide,
for a suitable time to treat said allergy, asthma and/or respiratory insufficiency.

2. The method according to claim 1, wherein said inulin and fructo-oligosaccharide are present in said composition in a weight ratio ranging from 25 to 0.05.

3. The method according to claim 1 wherein the composition is in the form of a sachet comprising powder, a capsule, a pill or a tablet.

4. The method according to claim 1, wherein the *B. breve* bacteria are selected from the group consisting of the strains *B. breve* Bb-03, *B. breve* M-16V, *B. breve* R0070, *B. breve* BRO3, *B. breve* BR92, *B. breve* DSM 20091, *B. breve* LMG 11613, *B. breve* YIT4065, *B. breve* FERM BP-6223 and *B. breve* CNCM 1-2219.

5. The method according to claim 1, wherein the human subject suffers from said dust mite allergy.

6. The method according to claim 1, wherein the human subject suffers from said dust mite induced asthma.

7. The method according to claim 1, wherein the human subject suffers from a respiratory tract infection.

8. The method according to claim 1, wherein administration of the composition reduces allergen-induced systemic production of IL-4, IL-5 and/or IL-13.

9. A method for increasing peak expiratory flow rate in a human subject suffering from dust mite allergy and/or dust mite-induced asthma, comprising administering to the subject an effective amount of a composition that comprises, based on dry weight of the composition:
    (a) at least $10^4$ cfu per gram *Bifidobacterium breve* bacteria that are not genetically modified, and
    (b) 0.25 to 5.5 wt % non-digestible oligosaccharides that include inulin and fructo-oligosaccharide,
for a suitable time to increase the peak expiratory flow rate.

10. The method according to claim 9, wherein said inulin and fructo-oligosaccharide are present in said composition in a weight ratio ranging from 25 to 0.05.

11. The method according to claim 9, wherein the composition is in the form of a sachet comprising powder, a capsule, a pill or a tablet.

12. The method according to claim 9, wherein the *B. breve* bacteria are selected from the group consisting of the strains *B. breve* Bb-03, *B. breve* M-16V, *B. breve* R0070, *B. breve* BRO3, *B. breve* BR92, *B. breve* DSM 20091, *B. breve* LMG 11613, *B. breve* YIT4065, *B. breve* FERM BP-6223 and *B. breve* CNCM 1-2219.

13. The method according to claim 9 wherein the human subject suffers from said dust mite allergy.

14. The method according to claim 9, wherein the human subject suffers from said dust mite induced asthma.

15. The method according to claim 9, wherein the human subject suffers from a respiratory tract infection.

16. The method according to claim 9, wherein administration of the composition reduces allergen-induced systemic production of IL-4, IL-5 and/or IL-13.

\* \* \* \* \*